US010136953B2

(12) United States Patent
Cattin et al.

(10) Patent No.: US 10,136,953 B2
(45) Date of Patent: Nov. 27, 2018

(54) COMPUTER ASSISTED SURGERY APPARATUS AND METHOD OF CUTTING TISSUE

(71) Applicant: ADVANCED OSTEOTOMY TOOLS—AOT AG, Basel (CH)

(72) Inventors: Philippe Cattin, Windisch (CH); Mathias Griessen, Steffisburg (CH); Adrian Schneider, Gunten (CH); Alfredo Bruno, Biel-Benken (CH)

(73) Assignee: Advanced Osteotomy Tools—AOT AG, Basel (CH)

( * ) Notice: Subject to any disclaimer, the term of this patent is extended or adjusted under 35 U.S.C. 154(b) by 198 days.

(21) Appl. No.: 14/900,822

(22) PCT Filed: Jun. 30, 2014

(86) PCT No.: PCT/EP2014/063790
§ 371 (c)(1),
(2) Date: Dec. 22, 2015

(87) PCT Pub. No.: WO2015/000822
PCT Pub. Date: Jan. 8, 2015

(65) Prior Publication Data
US 2016/0135906 A1    May 19, 2016

(30) Foreign Application Priority Data
Jul. 1, 2013   (EP) ..................................... 13174515

(51) Int. Cl.
*A61B 17/32* (2006.01)
*A61B 34/30* (2016.01)
(Continued)

(52) U.S. Cl.
CPC ............ *A61B 34/30* (2016.02); *A61B 18/201* (2013.01); *A61B 18/203* (2013.01); *A61B 34/20* (2016.02);
(Continued)

(58) Field of Classification Search
CPC ......... A61B 17/16; A61B 17/32; A61B 18/20; A61B 18/201; A61B 17/1622; A61B 18/203
See application file for complete search history.

(56) References Cited

U.S. PATENT DOCUMENTS

2004/0054248 A1*  3/2004  Kimchy ................. A61B 5/055
                                                                600/3
2012/0015329 A1   1/2012  Gross et al.
(Continued)

FOREIGN PATENT DOCUMENTS

JP      2012-059986 A    3/2012
WO    WO 2011/035792 A1  3/2011

OTHER PUBLICATIONS

Written Opinion of the International Searching Authority issued in PCT/EP2014/063790 dated Oct. 8, 2014.
(Continued)

*Primary Examiner* — Victor Nguyen
(74) *Attorney, Agent, or Firm* — Hoffman & Baron, LLP

(57) ABSTRACT

A computer assisted surgery apparatus includes a surgical instrument having an intervention member to cut tissue of a body part of a patient; a control unit arranged to control position and orientation of the intervention member in relation to the body part with regard to a predefined osteotomic line on the body part; and a tracking device arranged to track a position and orientation of the body part. The surgical instrument includes an optical monitoring system mounted in relation to the intervention member, wherein the optical
(Continued)

monitoring system is arranged to continuously detect positions of marks applied to the body part, and the control unit is arranged to adjust position and/or orientation of the intervention member when a predefined deviation of the positions of the marks is detected. The surgery apparatus allows for application of cuts in the body part at comparably complex cutting geometries and at comparably high precision.

16 Claims, 4 Drawing Sheets

(51) Int. Cl.
| | | |
|---|---|---|
| A61C 1/00 | (2006.01) | |
| A61B 18/20 | (2006.01) | |
| A61C 9/00 | (2006.01) | |
| A61C 1/08 | (2006.01) | |
| A61B 34/20 | (2016.01) | |
| A61B 18/00 | (2006.01) | |
| A61B 90/00 | (2016.01) | |

(52) U.S. Cl.
CPC ............ *A61C 1/0046* (2013.01); *A61C 1/082* (2013.01); *A61C 9/0053* (2013.01); *A61B 90/361* (2016.02); *A61B 2018/00565* (2013.01); *A61B 2018/00601* (2013.01); *A61B 2018/20359* (2017.05); *A61B 2034/2055* (2016.02); *A61B 2034/2065* (2016.02); *A61B 2090/0818* (2016.02); *A61B 2090/3735* (2016.02); *A61B 2090/3937* (2016.02)

(56) References Cited

U.S. PATENT DOCUMENTS

| | | |
|---|---|---|
| 2012/0061361 A1 | 3/2012 | Usuda et al. |
| 2013/0010081 A1 | 1/2013 | Tenney et al. |
| 2013/0035696 A1 | 2/2013 | Qutub |
| 2013/0096574 A1* | 4/2013 | Kang ................. A61B 17/1622 606/130 |

OTHER PUBLICATIONS

Notice of Reasons for Rejection issued in counterpart Japanese Application No. 2016-522553 dated Mar. 20, 2018.

\* cited by examiner

COMPUTER ASSISTED SURGERY APPARATUS AND METHOD OF CUTTING TISSUE

CROSS-REFERENCE TO RELATED APPLICATIONS

This application is the U.S. National Phase of International Patent Application No. PCT/EP2014/063790, filed on 30 Jun. 2014, which claims benefit of European Patent Application No. 13174515.0, filed on 1 Jul. 2013, the contents of which are incorporated herein by reference in their entirety.

TECHNICAL FIELD

The present invention relates to a computer assisted surgery apparatus and a method of computer assisted cutting of a tissue.

Such apparatus including a surgical instrument having an intervention member for cutting tissue of a body part of a patient, a control unit arranged to control a position and orientation of the intervention member of the surgical instrument in relation to the body part of the patient with regard to a predefined osteotomic line on the body part of the patient, and a tracking device arranged to track a position and orientation of the body part of the patient, can be used for cutting human or animal tissues and particularly human or animal bones.

BACKGROUND ART

In medical surgery, automated or semi-automated techniques are getting increasingly common for cutting human or animal tissue. For example, WO 2011/035792 A1 describes a computer assisted and robot guided laser osteotome medical device. This device uses a robot arm guided laser, such as an Er:YAG laser, to cut human or animal hard tissue, such as bone tissue, by photoablating the tissue along a predefined osteotomic line. Such a device can, e.g., allow for precise cutting of bone tissue which preciseness is increasingly demanded in many applications, for example, in the field of reconstructive surgery or the like.

Automated cutting tools or devices such as the device mentioned hereinbefore usually have tracking means by which position and orientation of target tissue and the laser head can be tracked. For example, today optical or magnetic tracking systems are used, which usually monitor the body part or tissue and the laser head, and detect deviations in position and/or orientation. For tracking, the body part and laser head are usually provided with appropriate marker shields or means recognizable by the tracking system.

Whereas classic cutting tools, such as saws and the like, have difficulty performing cutting geometries which are more complex than straight or slightly bent cuts, ablating bone with a laser allows for applying comparably complex cutting geometries. For example, with the device mentioned above, saw-tooth, dove-tail, and other specific cutting geometries with an associated functionality are possible. Cutting bones in such comparably complex geometries allows for a variety of new applications, e.g., in the field of reconstructive surgery and bone shaping.

However, the cutting widths possible with today's laser systems, which usually are in a range of 200 μm and smaller, pose high demands on the precision of the applied cuts. Minor geometrical errors in an applied cut can prevent proper application such as reassembling of cut bone pieces, for example, after shifting them with regard to each other. If, for example, the body part of the patient moves during the cutting process or when the cutting process is interrupted by, e.g., the surgeon, laser guiding means such as the robot has to be able to automatically reposition with high accuracy to continue the cutting process.

Today's optical or magnetic tracking systems are, however, not accurate enough as their best precision is usually in the range of 200 μm, which is not suitable compared to what, e.g., is required for robot-guided laser osteotomy. In addition thereto, today's robots or similar means are capable of moving with a preciseness up to about 200 μm. Thus, the overall preciseness of robot and tracking system are together not appropriate for many applications.

Therefore, there is a need for an automatic or a semi-automatic surgery apparatus and method allowing application of cuts in human or animal hard tissue with comparably complex geometries at a comparably high precision.

In particular, there is a need for providing a sufficiently precise movement of a cutting instrument, such as a laser beam, in relation to a tissue to cut such that comparably complex cutting geometries are applicable.

SUMMARY

According to the invention this need is settled by a computer assisted surgery apparatus as it is defined by the features of independent claim 1, and by a method of computer assisted cutting of a tissue as it is defined by the features of independent claim 12. Preferred embodiments are subject of the dependent claims.

In particular, the invention deals with a computer assisted surgery apparatus including a surgical instrument having an intervention member for cutting tissue of a body part of a patient; a control unit arranged to control a position and orientation of the intervention member of the surgical instrument in relation to the body part of the patient with regard to a predefined osteotomic line on the body part of the patient; and a tracking device arranged to track a position and orientation of the body part of the patient. Further, the surgical instrument of the apparatus includes an optical monitoring system being fixedly mounted in relation to the intervention member of the surgical instrument, wherein the optical monitoring system is arranged to continuously detect positions of natural landmarks on the human or animal hard tissue or marks applied to the body part of the patient, and the control unit is arranged to adjust position and/or orientation of the intervention member of the surgical instrument when a predefined deviation of the positions of the marks is detected.

In the context of the invention, the term "patient" relates to human beings and also to animals. The term "tissue" in connection with the present invention can relate to human or animal tissue and preferably to hard tissue such as nail tissue and particularly bone tissue. The term "body part" can relate to any suitable body part of the patient which is to be cut by the apparatus. In particular, it can relate to any bone such as the maxilla or upper jaw, mandibula or lower jaw, skull or the like of the patient. The term "osteotomic line" can relate to a line along which the body part is to cut. It can particularly define the geometry of the cut. The geometry of the cut can, e.g., be planned by a computer evaluating data of the body part, e.g., gathered by imaging technology such as optical coherence tomography (OCT). In such planning of the cut, the computer can also calculate the osteotomic line.

The control unit can include a computer which can be equipped with a hard disk, a central processing unit, a random access memory, a read only memory, and the like. The computer can, e.g., be a personal computer, a laptop computer, or the like. The optical monitoring system can particularly be or can include a different entity or unit than the tracking device such that the optical monitoring system is at least partially distinct from the tracking device. The monitoring system can, e.g., be fixedly mounted in relation to the intervention member by being directly or indirectly connected to the intervention member in a rigid manner. For example, it can be screwed, bonded, or otherwise rigidly mounted to the surgical instrument. The term "deviation" in context of the position of the marks can relate to a difference between the detected position of the marks and an expected position of the marks, wherein the expected position can be calculated in accordance with a previous position of the marks and a movement of the intervention member in relation to the body part.

In addition to the overall picture of the surgery situation provided by the tracking device, the optical monitoring system allows for specifically controlling the cutting process with regard to the osteotomic line. In particular, the optical monitoring system allows providing data of the cutting process at a comparably high precision. By fixedly mounting the monitoring system in relation to the intervention member of the surgical instrument, a respective deviation can be excluded and precision of the overall controlling can be increased accordingly. The monitoring system can be adjusted to provide detailed information or a detailed picture of a comparably small section or window at a comparably high resolution. Also, focusing on the natural landmarks or marks which can be specifically applied to the body part with the aim to monitor the osteotomic line or cut, the monitoring system allows to further be tailored for a high precision control of the cutting process. Thus, the apparatus according to the invention allows for application of cuts in the body part with comparably complex cutting geometries at comparably high precision.

For example, the invention can be used by using natural visible landmarks or point landmarks as on the applied cut or osteotomic line itself as marks or by applying, e.g., lasing, additional artificial marks onto the body part such as a bone to be cut in the vicinity of the planned cut or osteotomic line. For longer cuts, multiple sets of these marks (landmarks visible on the cut or osteotomic line itself or additionally applied marks) can be applied along the path of the cut, i.e., the osteotomic line. Using the monitoring system with, e.g., one or preferably two cameras, these marks can be automatically detected. If multiple marks are visible or detectable by the monitoring system, their three-dimensional position can be determined, e.g., within a monitoring system coordinate system. Or, similarly, the exact position of the monitoring system with respect to these points can be calculated. As the monitoring system is rigidly or fixedly connected with regard to the intervention member and can be calibrated, the exact position of the intervention member with respect to the marks can be calculated. As the monitoring system and, e.g., its cameras can have a comparably small field-of-view with a high pixel resolution, the positions relative to the monitoring system can be determined with high accuracy. In a particular embodiment, the field-of-view is 1 cm in square and the resolution is 1,000 pixels in square. Such a setup would yield a positional accuracy in the range of 10 μm, being accurate enough for many applications of the apparatus.

Alternatively, for example, an optical coherence tomography (OCT) probe in cooperation with a scanning mirror of a laser head as surgical instrument could be used to create a three-dimensional map of the body part around the cut or osteotomic line. Natural landmarks, landmarks from the applied cut and potentially artificially created landmarks can then be used to determine the relative position of the laser head with respect to the body part.

Alternatively, for example, a light source visible to at least one of the cameras can be used to create a three-dimensional map of the body part around the cut or osteotomic line. Natural landmarks, landmarks from the applied cut, and potentially artificially created landmarks can then be used to determine the relative position of the laser head with respect to the body part.

Alternatively, the stereo camera setup can be used to create a three-dimensional map of the body part around the cut, or osteotomic line. Natural landmarks, landmarks from the applied cut, and potentially artificially created landmarks can then be used to determine the relative position of the laser head with respect to the body part.

Preferably, the control unit is arranged to calculate expected positions of the marks based on the positions of marks applied to the body part of the patient detected by the optical monitoring system. These detected positions of the marks preferably are used to calculate the relative position of the tissue to the intervention member. By calculating expected positions and evaluating detected positions, the control unit allows for efficiently controlling the cutting process. In particular, comparably small deviations of the positions with respect to the osteotomic line can be detected and respective precise adjustments, e.g., to the intervention member, can be performed in order to continuing precisely cutting the body part.

Preferably, the control unit is arranged to calculate expected positions of the marks based on previous positions of the marks and movement of the intervention member in relation to the body part, wherein the predefined deviation of the positions of the marks is detected when the expected positions of the marks differ from corresponding positions of marks detected by the optical monitoring system. Such arrangement of the control unit allows for efficiently controlling the cutting process.

Preferably, the surgical instrument includes a marking member being arranged to apply the marks to the body part of the patient during operation in which the body part of the patient is cut along the osteotomic line by the intervention member of the surgical instrument. In this context, the term "marking member" can relate to any means suitable for applying marks to the body part intended for monitoring the cutting process with regard to the osteotomic line. It can, e.g., be arranged to apply dots or lines on the body part near or at the osteotomic line. Such a marking member allows for precisely applying marks which are specifically arranged and shaped for the purpose of controlling the osteotomic line. Like this, precision and efficiency of such controlling can be comparably high.

Preferably, the computer assisted surgery apparatus further includes a robot arm, wherein the surgical instrument is mounted to the robot arm and the control unit is arranged to control movement of the robot arm in order to control the position and orientation of the surgical instrument in relation to the body part of the patient. Such a robot arm allows for efficiently adjusting position and/or orientation of the intervention member with respect to the body part in all degrees of freedom of the movement of the intervention member at a comparably high precision.

Preferably, the intervention member includes a laser source. Such a laser source allows for providing a laser beam onto the body part for cutting the body part. Laser induced cutting makes it possible to precisely cut the body part at comparably complex cutting geometries. Thereby, the intervention member preferably a focusing optics and a beam redirector. By means of such a focusing optics and beam redirector, the laser beam can precisely be provided onto the body part such that the body part can precisely be cut. Thereby, the beam redirector can particularly include one or more mirrors or the like.

Preferably, the intervention member of the surgical instrument is identical to the marking member of the surgical instrument. The surgical instrument can in that case be arranged to apply marks from time to time. For example, if the surgical instrument includes a laser source, the laser source can apply laser shots to create holes as marks at specific positions on the body part. In particular, these specific positions can be near or on the osteotomic line.

Preferably, the optical monitoring system of the surgical instrument includes at least one camera and preferably two cameras. Such at least one camera can be used to observe the marks, wherein using two cameras allows for providing a three-dimensional picture of the marks and the body part. Since the cameras are fixedly mounted in relation to the intervention member of the surgical instrument, the marks can be precisely observed and monitored, and the cutting process along the osteotomic line can precisely be controlled.

Preferably, the tracking device includes a camera. Thereby, the at least one camera of the optical monitoring system of the surgical instrument preferably is adjusted to cover a monitoring area of the tissue of the body part of the patient around a spot where the intervention member of the surgical instrument acts on the body part of the patient, the camera of the tracking device preferably is adjusted to cover an overview area of the body part of the patient, and the monitoring area preferably is smaller than the overview area. Thus, the camera of the tracking device is less focused than the at least one camera of the monitoring system, such that the tracking device can provide an overview of the situation and the monitoring system can precisely monitor the cutting process along the osteotomic line.

Another aspect of the invention relates to a method of computer assisted cutting of a tissue, including predefining an osteotomic line on the tissue; automatically controlling position and orientation of an intervention member of a surgical instrument such that the tissue is cut along the osteotomic line; and tracking a position of the tissue. In the method according to the invention, positions of marks applied to the tissue are continuously detected by an optical monitoring system being fixedly mounted in relation to the intervention member of the surgical instrument, and the position and/or orientation of the intervention member of the surgical instrument is adjusted when a predefined deviation of the positions of the marks is detected. The method can be applied in vitro.

Corresponding to the apparatus according to the invention, the method according to the invention allows for applying cuts in the body part at comparably complex cutting geometries and at comparably high precision. Also, the further effects and advantages of the preferred embodiments of the apparatus described above can be implemented by corresponding preferred embodiments of the method as described hereinbelow.

Preferably, the marks are calculated based on the positions of marks applied to the body part of the patient detected by the optical monitoring system, wherein these detected positions of the marks are used to calculate the relative position of the tissue to the intervention member.

Preferably, expected positions of the marks are calculated based on previous positions of the marks and a movement of the intervention member in relation to the body part, wherein the predefined deviation of the positions of the marks is detected when the expected positions of the marks differ from corresponding positions of marks detected by the optical monitoring system.

Preferably, the marks are applied to the tissue during cutting of the tissue along the osteotomic line, or well visible natural landmarks are chosen in addition.

Preferably, the intervention member includes a laser source and the tissue is cut by photoablation via a laser beam induced by the laser source. Thereby, the laser beam preferably is focused by a focusing optics and redirected by a beam redirector.

Preferably, the marks are applied to the tissue by the intervention member of the surgical instrument. Preferably, at least one camera and preferably two cameras of the optical monitoring system of the surgical instrument continuously detect the positions of the marks.

Preferably, the position of the tissue is tracked by a camera. Thereby, the at least one camera of the optical monitoring system of the surgical instrument preferably is adjusted to cover a monitoring area of the tissue of the body part of the patient around a spot where the intervention member of the surgical instrument acts on the tissue, and the monitoring area preferably is smaller than the overview area to which the camera tracking the position of the tissue is adjusted.

These and other aspects of the invention will be apparent from and elucidated with reference to the embodiment(s) described hereinafter.

BRIEF DESCRIPTION OF THE DRAWINGS

The computer assisted surgery apparatus and the method of computer assisted cutting of a tissue according to the invention are described in more detail hereinbelow by way of example embodiments and with reference to the attached drawings, in which.

DETAILED DESCRIPTION

Figure 1:
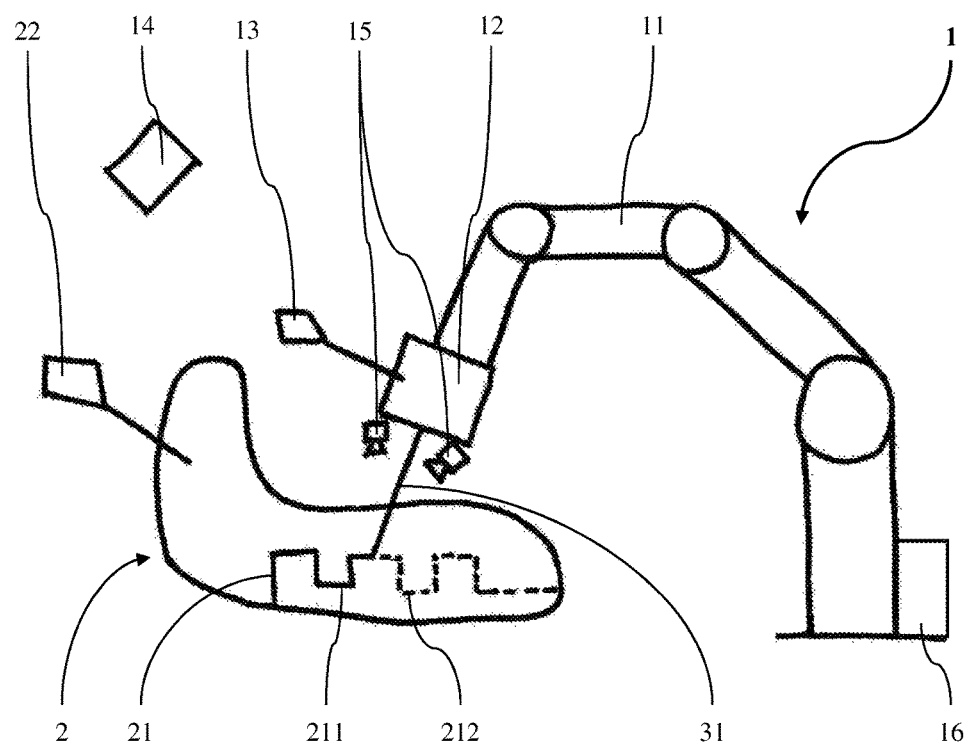
FIG. 1 shows a first embodiment of a computer assisted surgery apparatus in accordance with the invention and a mandibula with a first embodiment of an osteotomic line.

FIG. 1 shows a schematic view of a first embodiment of a computer assisted surgery apparatus 1. The apparatus 1 includes a robot arm 11 being fixedly arranged at its one longitudinal end on a support platform. On the other longitudinal end of the robot arm a laser head 12 as a surgical instrument is arranged which is movable by the robot arm 11 in all degrees of freedom. The laser head 12 has a laser source, a focusing optics and a beam redirector. Fixedly mounted to the laser head 12 is a monitoring system of the laser head 12 having two cameras 15. Furthermore, a marker shield 13 is attached to the laser head 12. The apparatus 1 also includes a tracking device 14 and a control unit having a computer 16.

In the sphere of action of the apparatus 1, a mandibula 2 or lower jaw as body part of a patient or tissue is arranged. A marker shield 22 is attached to the mandibula. The laser head 12 of the apparatus provides a laser beam 31 as an intervention member onto the mandibula 2 along an osteotomic line 21. Thereby, the mandibula 2 is cut by the laser beam 31 along the osteotomic line 21. The osteotomic line 21 has a realized portion 211, i.e., the cut, in which the mandibula 2 is cut by the laser beam 31 already and a planned portion 212 in which the mandibula 2 still is to be cut. The osteotomic line 21 has a periodic rectangular shape with right angles such that plural parallel bars and recesses are formed in the mandibula 2.

In use of the apparatus 1, the osteotomic line 21 is predefined on the mandibula 2. This can be performed electronically such as by obtaining data of the precise shape and condition of the mandibula 21, e.g., by optical coherence tomography (OCT) and by modeling and calculating the osteotomic line 21 on the mandibula 2 in a computer, which can be the computer 16 of the control unit. The apparatus 1 and particularly computer 16 is configured appropriately and the mandibula 2 is arranged at a suitable location in the sphere of action of the apparatus 1.

The laser beam 31 provided by the laser head 12 then cuts the mandibula 2 along the osteotomic line 21, wherein for that purpose the laser head 12 is moved by the robot arm 11. The position and orientation of the laser beam 31 is automatically controlled by the control unit such that the mandibula 2 is precisely cut along the osteotomic line 21.

The tracking device 14 captures the marker shield 13 of the laser head 12 and the marker shield 22 of the mandibula 2. For that purpose, the tracking device can, e.g., be equipped with a camera being focused to have both marker shields 13 and 22 in its view. In application with the mandibula 2, such view can have a dimension of approximately 20 cm to 50 cm in square. The marker shields 13 and 22 have geometric characteristics which are easily identifiable via the tracking device 14. Like this, the overall position of the mandibula 2 and the apparatus 1 is tracked and monitored by the tracking device 14.

Before and while the mandibula 2 is cut, the apparatus 1 continuously applies marks near or on the planned or realized osteotomic line 21, wherein it is assured that always at least three marks are in focus of the two cameras 15 of the monitoring system. These two cameras 15 are adjusted such that their focus covers a view of about 0.5 cm to 3 cm in square and preferably about 1 cm in square or 1.5 cm in square. The resolution of the camera can be at least about 500 pixels in square preferably 1'000 pixels in square or more. For applying the marks, the laser head 12 provides laser beam 31 shots which photoablate small holes in the mandibula 2. Thereby, the laser head 12 and the laser beam 31 act as a marking member. These small holes are the marks positioned near or on the osteotomic line 21.

The positions of the small holes are continuously detected by the cameras 15 of the optical monitoring system and evaluated by the computer 16 of the control unit. When a predefined deviation of the positions of the small holes is detected by the control unit, the position and/or orientation of the laser head 12 and, thus, of the laser beam 31 is corrected by adjusting the robot arm 11.

Figure 2:
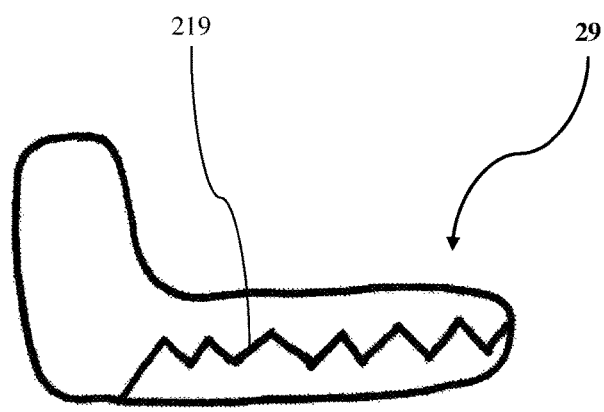
FIG. 2 shows a side view of a mandibula with a second embodiment of an osteotomic line.

In FIG. 2, a mandibula 29 with a second embodiment of an osteotomic line 219 is shown. Thereby, the osteotomic line 219 has a periodic triangular shape such that a saw like structure is formed in the mandibula 29.

Figure 3:
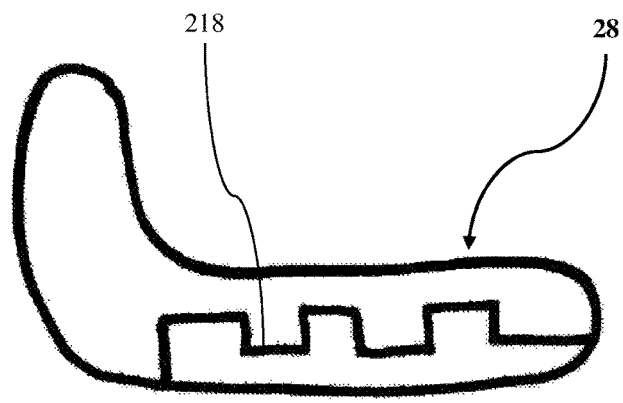
FIG. 3 shows a side view of a mandibula with a third embodiment of an osteotomic line.

FIG. 3 shows a mandibula 28 with a third embodiment of an osteotomic line 218. The osteotomic line 218 has a periodic rectangular shape such that plural bars and recesses are formed in the mandibula 28.

Figure 4:
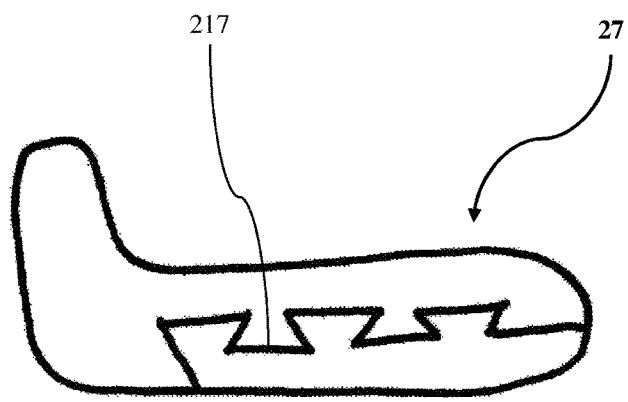
FIG. 4 shows a side view of a mandibula with a fourth embodiment of an osteotomic line.

In FIG. 4, a mandibula 27 with a fourth embodiment of an osteotomic line 217 is shown. Thereby, the osteotomic line 217 has a periodic trapezoid or dove-tail shape.

Figure 5:
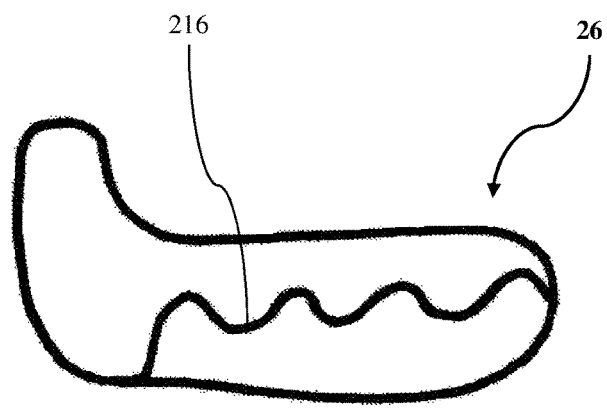
FIG. 5 shows a side view of a mandibula with a fifth embodiment of an osteotomic line.

FIG. 5 shows a mandibula 26 with a fifth embodiment of an osteotomic line 216. The osteotomic line 216 has a sinusoidal shape such that a wave-like structure is formed in the mandibula 26.

Figure 6:
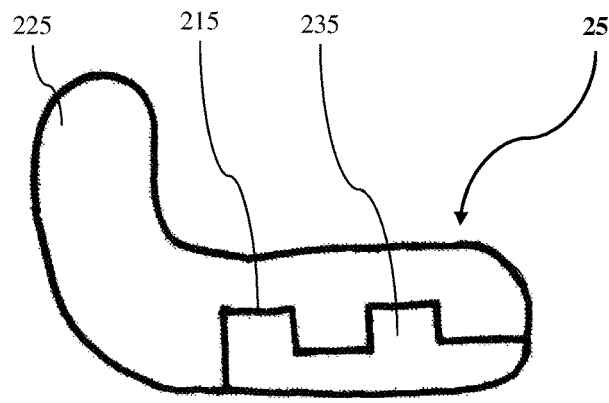
FIG. 6 shows a side view of a mandibula with a sixth embodiment of an osteotomic line.

In FIG. 6, a mandibula 25 with a sixth embodiment of an osteotomic line 215 is shown. The osteotomic line 215 has a periodic rectangular shape similar to the osteotomic line 21 of mandibula 2 of FIG. 1 and the osteotomic line 218 of mandibula 28 of FIG. 3. The mandibula 25 is cut apart along the osteotomic line 215 such that it is divided in an upper portion 225 and a lower portion 235.

Figure 7:
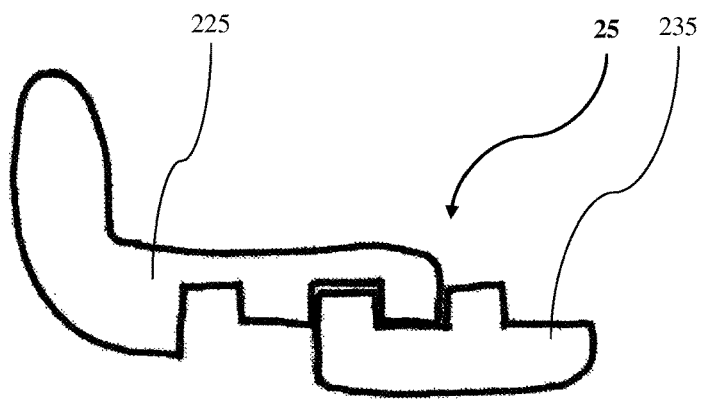
FIG. 7 shows a side view of the mandibula of FIG. 6 being repositioned.

FIG. 7 shows the mandibula 25 of FIG. 6, wherein the upper portion 225 and the lower portion 235 are separated from each other and reassembled. Thereby, the lower portion 235 of the mandibula 25 is longitudinally shifted with regard to the upper portion 225 by one bar or recess such that the bars of the lower portion 235 are arranged in recesses of the upper portion 225 neighboring the recesses from which they originate. Like this the mandibula 25 can be reshaped in an exactly predefined manner and the target position of the upper portion 225 and the lower portion 235 of the mandibula 25 can be structurally predefined. A slight or continuous shifting of the upper portion 225 in relation to the lower portion 235 is not possible.

Figure 8:
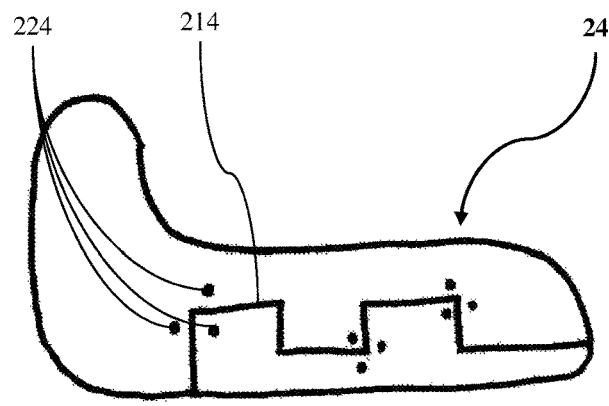
FIG. 8 shows a side view of a mandibula with a first embodiment of marks.

In FIG. 8, a mandibula 24 with a seventh embodiment of an osteotomic line 214 is shown. The osteotomic line 214 again has a periodic rectangular shape similar to the osteotomic line 21 of mandibula 2 of FIG. 1, the osteotomic line 218 of mandibula 28 of FIG. 3, and the osteotomic line 215 of mandibula 25 of FIG. 6. The mandibula 24 has plural groups of marks 224 wherein each group has three marks 224 being arranged close to the osteotomic line 214.

Figure 9:
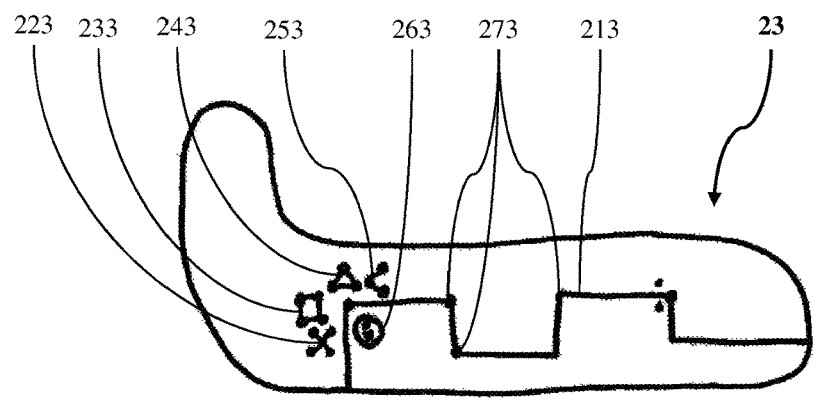
FIG. 9 shows a side view of a mandibula with plural further embodiments of marks.

FIG. 9 shows a mandibula 23 with an eighth embodiment of an osteotomic line 213 is shown. The osteotomic line 213 again has a periodic rectangular shape similar to the osteotomic line 21 of mandibula 2 of FIG. 1, the osteotomic line 218 of mandibula 28 of FIG. 3, the osteotomic line 215 of mandibula 25 of FIG. 6, and the osteotomic line 214 of mandibula 24 of FIG. 8. The mandibula 23 has plural groups of marks, wherein each group is an example of a possible arrangement of marks in order to be capable of being monitored in a preferred manner. In a first group, five marks 223 are arranged in the shape of a cross, wherein at the end of the cross as well as at the intersection, one of the marks 224 is provided. In a second group, four marks 233 are arranged at the corners of a square. In a third group, three marks 243 are arranged at the corners of an equilateral triangle. In a fourth group, three marks 253 are arranged at the corner and at the end of two angled legs. In a fifth group, two marks 263 are arranged inside a circle. In a sixth group, plural marks 273 are arranged on landmark points of the osteotomic line 213 itself, wherein these landmark points preferably are positioned at particular characterizing spots of the osteotomic line 213, such as at angles or the like.

Figure 10:
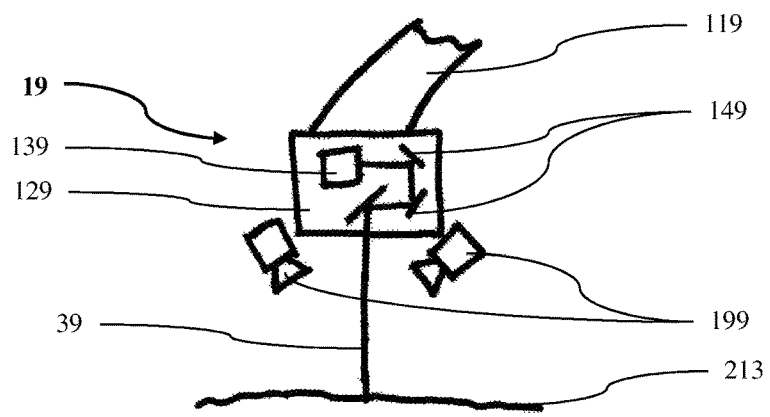
FIG. 10 shows a second embodiment of a computer assisted surgery apparatus in accordance with the invention.

In FIG. 10, a schematic view of a second embodiment of a computer assisted surgery apparatus 19 is shown. The apparatus 19 includes a robot arm 119. On one longitudinal end of the robot arm 119 a laser head 129 as surgical instrument is arranged which is movable by the robot arm 119 in all degrees of freedom. The laser head 129 has a laser source 139, a focusing optics and three mirrors 149 as a beam redirector. A monitoring system of the laser head 129 having two cameras 199 is fixedly mounted to the laser head 129. The laser source 139 provides a laser beam 39 which is redirected by the mirrors 149 and applied along an osteotomic line 213 generating a cut.

Using the laser head 129 and the two calibrated cameras 199 allows to directly determining the three-dimensional coordinates of marks applied on or around the osteotomic line 213 or cut. In this set-up, three recognizable and in their three-dimensional configuration known points or marks are enough to determine the relative position of the laser head 129 with respect to the body part.

The exact shape of the marks is unimportant, as long as a minimum of three point marks with their known three-dimensional configuration can be differentiated by the two cameras 199. These points can be arranged as shown above, e.g., as the corners of a square, triangle, cross, or the enter of a shape such as a circle/ellipse, or even edges of the already applied cut or a combination thereof. The three-dimensional position of these point marks has to be determined with the cameras 199 and stored prior to any relative position change of the body part and surgical laser head 129. A pattern that causes the least amount of tissue damage is preferred, thus the preferred embodiment are three small dots as marks using a two camera set-up or six small dots in a one camera set-up as described below. In addition, by using the corner of the osteotomic line 213 or cut as a mark, it is even possible to live with only two additional lased points.

In use, a possible cutting process can be as follows: The robot is referenced with the patient using the optical tracking system. The robot arm 119 moves to the targeted bone or body part and stops. Using the steerable mirrors 149 in the laser head 129, artificial landmarks or marks (e.g., dots) are lased into the bone (as needed) using the same laser as used for the cutting process with, however, a very low photon dosage to limit damage to the tissue. Using the steerable mirrors 149, the laser head 129 then starts performing the planned cut along the osteotomic line 213. By continuously observing the landmarks with the cameras 199, any relative positional change of the body part or robot arm 119 can be immediately detected. When such a positional change is detected, e.g., the body part or patient moved or the robot was manually displaced, the laser beam 39 is stopped immediately. Using positional information from a tracking device or from observing the artificial marks, the robot arm 119 can then be repositioned again over the body part. Using the positional information from the marks and integrated cameras 199, the relative position of the laser beam 39 with respect to the patient's body part can be accurately determined. Any remaining positional errors can then be compensated using the steerable mirrors 149 or using the robot arm 119, given that its relative position control is good enough. Once the cut has been performed, the robot arm 119 moves to the next location and applies a new pattern of artificial marks. For comparably long cuts, it might be necessary to repeat this process multiple times, i.e., several patterns at different locations are lased into the body part.

Figure 11:
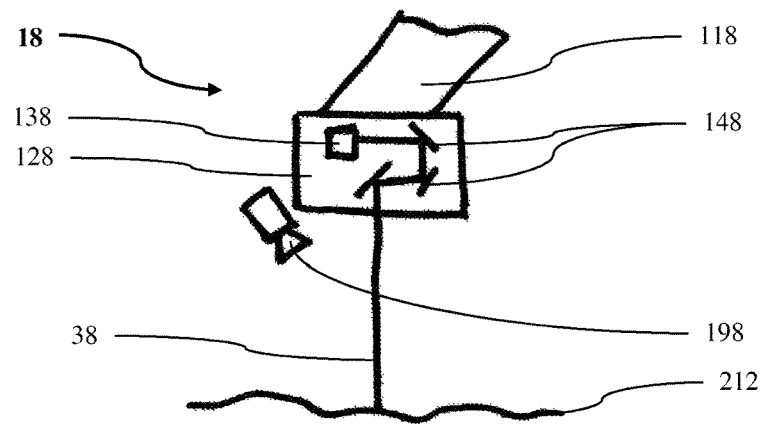
FIG. 11 shows a third embodiment of a computer assisted surgery apparatus in accordance with the invention.

FIG. 11 shows a schematic view of a third embodiment of a computer assisted surgery apparatus 18. The apparatus 18 includes a robot arm 118 which is fixedly connected to a laser head 128 as surgical instrument at its one longitudinal end. The laser head 128 is movable by the robot arm 118 in all degrees of freedom. The laser head 128 has a laser source 138, a focusing optics and three mirrors 148 as a beam redirector. A monitoring system of the laser head 128 having one camera 198 is fixedly mounted to the laser head 128. The laser source 138 provides a laser beam 38 which is redirected by the mirrors 148 and applied along an osteotomic line 212 generating a cut.

In the simplified set-up of FIG. 11 only one camera 198 is used for the localization of the marks. If the camera 198 and the laser head 128 are calibrated, the three-dimensional position of the marks can be determined by triangulation directly after they have been applied or lased into the bone. In order for the camera 198 to determine its relative position with respect to these marks at least six point marks have to be visible assuming non-planar surfaces. This in contrast to the two camera set-up where only three visible marks are required.

While the invention has been illustrated and described in detail in the drawings and foregoing description, such illustration and description are to be considered illustrative or exemplary, and not restrictive. It will be understood that changes and modifications may be made by those of ordinary skill within the scope and spirit of the following claims. In particular, the present invention covers further embodiments with any combination of features from different embodiments described above and below. For example, it is possible to operate the invention in an embodiment wherein:

An OCT probe can be used in cooperation with a two-dimensional scanning mirror to map at least part of visible surface of the body part in the vicinity around the osteotomic line or cut. Visible natural and/or artificial marks can then be used to determine the relative position of the surgical instrument or laser head with respect to the body part.

A combination of natural landmarks and artificial landmarks visible in a camera image or in OCT data can be used to determine the relative position of the laser head with respect to the bone.

The invention also covers all further features shown in the figures individually, although they may not have been described in the previous or following description. Also, single alternatives of the embodiments described in the figures and the description and single alternatives of features thereof can be disclaimed from the subject matter of the invention or from disclosed subject matter. The disclosure includes subject matter consisting of the features defined in the claims or the example embodiments as well as subject matter including these features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

The present disclosure does also includes the following further embodiments:

Embodiment 1 is a method of computer assisted cutting of a tissue or of controlling computer assisted cutting of a tissue including: predefining an osteotomic line on the tissue; automatically controlling a position and orientation of an intervention member of a surgical instrument such that the tissue is cut along the osteotomic line; and tracking a position of the tissue, wherein positions of marks applied to the tissue are continuously detected by an optical monitoring system being fixedly mounted in relation to the intervention member of the surgical instrument, wherein the position and/or orientation of the intervention member of the surgical instrument is adjusted when a predefined deviation of the positions of the marks is detected or data about the position and/or orientation of the intervention member of the surgical instrument is provided for adjustment when a predefined deviation of the positions of the marks is detected. The method can be an in vitro method.

Embodiment 2 is the method of embodiment 1, wherein expected positions of the marks are calculated based on the positions of marks applied to the body part of the patient detected by the optical monitoring system, wherein the detected positions of the marks are used to calculate the relative position of the tissue to the intervention member.

Embodiment 3 is the method of embodiment 1 or 2, wherein expected positions of the marks are calculated based on previous positions of the marks and a movement of the intervention member in relation to the body part, wherein the predefined deviation of the positions of the marks is detected when the expected positions of the marks differ from corresponding positions of marks detected by the optical monitoring system.

Embodiment 4 is the method of any one of embodiments 1 to 3, wherein the marks are applied to the tissue during cutting of the tissue along the osteotomic line.

Embodiment 5 is the method of any one of embodiments 1 to 4, wherein the intervention member includes a laser source and the tissue is cut by photoablation via a laser beam induced by the laser source.

Embodiment 6 is the method of any one of embodiments 1 to 5, wherein the laser beam is focused by a focusing optics and redirected by a beam redirector.

Embodiment 7 is the method of any one of embodiments 1 to 6, wherein the marks are applied to the tissue by the intervention member of the surgical instrument.

Embodiment 8 is the method of any one of embodiments 1 to 7, wherein at least one camera and preferably two cameras of the optical monitoring system of the surgical instrument continuously detect the positions of the marks.

Embodiment 9 is the method of any one of embodiments 1 to 8, wherein the position of the tissue is tracked by a camera.

Embodiment 10 is the method of any one of embodiments 1 to 9, wherein the at least one camera of the optical monitoring system of the surgical instrument is adjusted to cover a monitoring area of the tissue of the body part of the patient around a spot where the intervention member of the surgical instrument acts on the tissue and the monitoring area is smaller than the overview area to which the camera tracking the position of the tissue is adjusted.

The invention claimed is:

1. A computer assisted surgery apparatus, the apparatus comprising:
 a surgical instrument having an intervention member to cut tissue of a body part of a patient;
 a control unit arranged to automatically control position and orientation of the intervention member of the surgical instrument in relation to the body part of the patient with regard to a predefined osteotomic line on the body part of the patient; and
 a tracking device arranged to track a position and orientation of the body part of the patient,
 wherein the surgical instrument comprises an optical monitoring system being fixedly mounted in relation to the intervention member of the surgical instrument, the optical monitoring system being arranged to continuously detect positions of marks applied to the body part of the patient, and
 wherein the control unit is arranged to adjust position or orientation, or position and orientation of the intervention member of the surgical instrument when a predefined deviation of the positions of the marks is detected.

2. The computer assisted surgery apparatus according to claim 1, wherein the control unit is arranged to calculate expected positions of the marks based on the positions of marks applied to the body part of the patient detected by the optical monitoring system and wherein these detected positions of the marks are used to calculate the relative position of the tissue to the intervention member.

3. The computer assisted surgery apparatus according to claim 1, wherein the control unit is arranged to calculate expected positions of the marks based on previous positions of the marks and a movement of the intervention member in relation to the body part, and wherein the predefined deviation of the positions of the marks is detected when the expected positions of the marks differ from corresponding positions of marks detected by the optical monitoring system.

4. The computer assisted surgery apparatus according to claim 1, wherein the surgical instrument comprises a marking member being arranged to apply the marks to the body part of the patient during operation in which the body part of the patient is cut along the osteotomic line by the intervention member of the surgical instrument.

5. The computer assisted surgery apparatus according to claim 4, wherein the intervention member of the surgical instrument is identical to the marking member of the surgical instrument.

6. The computer assisted surgery apparatus according to claim 1, wherein the apparatus further comprises a robot arm, and wherein the surgical instrument is mounted to the robot arm and the control unit is arranged to control a movement of the robot arm in order to control the position or orientation, or the position and orientation of the surgical instrument in relation to the body part of the patient.

7. The computer assisted surgery apparatus according to claim 1, wherein the intervention member comprises a laser source.

8. The computer assisted surgery apparatus according to claim 7, wherein the intervention member comprises a focusing optics and a beam redirector.

9. The computer assisted surgery apparatus according to claim 1, wherein the optical monitoring system the surgical instrument comprises at least one camera.

10. The computer assisted surgery apparatus according to claim 9, wherein at least one camera of the optical monitoring system of the surgical instrument is adjusted to cover a monitoring area of the tissue of the body part of the patient around a spot where the intervention member of the surgical instrument acts on the body part of the patient, and wherein a the camera of the tracking device is adjusted to cover an overview area of the body part of the patient, and the monitoring area is smaller than the overview area.

11. The computer assisted surgery apparatus according to claim 9, wherein the optical monitoring system of the surgical instrument comprises two cameras.

12. The computer assisted surgery apparatus according to claim 1, wherein the tracking device comprises a camera.

13. A method of computer assisted cutting of a tissue, the method comprising:
predefining an osteotomic line on the tissue;
automatically controlling position and orientation of an intervention member of a surgical instrument such that the tissue is cut along the osteotomic line;
tracking a position of the tissue;
continuously detecting positions of marks applied to the tissue by an optical monitoring system, the optical monitoring system being fixedly mounted in relation to the intervention member of the surgical instrument; and
adjusting the position or orientation, or the position and orientation of the intervention member of the surgical instrument when a predefined deviation of the positions of the marks is detected.

14. The method according to claim 13, wherein the method further comprises:
calculating expected positions of the marks based on the positions of marks applied to the body part of the patient detected by the optical monitoring system; and
calculating the relative position of the tissue to the intervention member using the positions of the marks detected by the optical monitoring system.

15. The method according to claim 13, wherein the method further comprises:
calculating expected positions of the marks based on previous positions of the marks and movement of the intervention member in relation to the body part; and
detecting the predefined deviation of the positions of the marks when the expected positions of the marks differ from corresponding positions of marks detected by the optical monitoring system.

16. The method according to claim 13, wherein the method further comprises applying the marks to the tissue during cutting of the tissue along the osteotomic line.

* * * * *